United States Patent [19]

Masano

[11] Patent Number: 5,441,049

[45] Date of Patent: Aug. 15, 1995

[54] CONDUCTIVITY METER

[75] Inventor: Thomas M. Masano, Scottsdale, Ariz.

[73] Assignee: Automata Medical Instrumentation, Inc., Scottsdale, Ariz.

[21] Appl. No.: 997,334

[22] Filed: Dec. 28, 1992

[51] Int. Cl.$^6$ .................. A61B 5/00; G01N 27/02
[52] U.S. Cl. .................................. 128/635; 324/446
[58] Field of Search ............... 128/632, 633, 635, 637, 128/734, 736, 763, 765, 770, 771; 604/38, 51, 52, 404; 204/409, 411; 324/439, 441, 444, 446, 449, 450

[56] References Cited

U.S. PATENT DOCUMENTS

| | | | |
|---|---|---|---|
| 3,582,768 | 6/1971 | Watson et al. | 324/449 |
| 4,137,494 | 1/1979 | Malley et al. | 204/409 |
| 4,275,352 | 6/1981 | Sudar et al. | 324/449 X |
| 4,553,552 | 11/1985 | Valdespino et al. | 128/635 |
| 4,808,930 | 2/1989 | Kaiser | 324/441 X |
| 4,835,477 | 5/1989 | Polaschegg et al. | 324/441 X |
| 4,863,873 | 9/1989 | Matson | 204/411 X |
| 4,891,575 | 1/1990 | Kogo et al. | 324/446 X |
| 5,046,496 | 9/1991 | Betts et al. | 204/409 X |
| 5,066,859 | 11/1991 | Karkar et al. | 128/633 |
| 5,150,037 | 9/1992 | Kouzuki | 324/446 X |
| 5,165,406 | 11/1992 | Wong | 204/409 X |
| 5,176,144 | 1/1993 | Yoshikoshi et al. | 128/692 |
| 5,194,814 | 3/1993 | D'Couto | 324/446 |

*Primary Examiner*—Lee S. Cohen
*Assistant Examiner*—Samuel Gilbert
*Attorney, Agent, or Firm*—Cahill, Sutton & Thomas

[57] ABSTRACT

A conductivity meter includes a cell having a passageway through which dialysate flows during measurement. A constriction in the passageway meters the flow and partially defines the cell constant. To measure conductivity, an alternating current is applied to the dialysate through cylindrical electrodes in the passageway on each side of the constriction. A thermistor adjacent one of the electrodes is used to measure the temperature of the dialysate. A housing for the cell includes an elongated handle and an enlarged portion, containing the cell, extending to one side of the handle. The handle contains a printed circuit board having circuitry for making the measurement and the enlarged portion includes a window for display of the measurement.

11 Claims, 2 Drawing Sheets

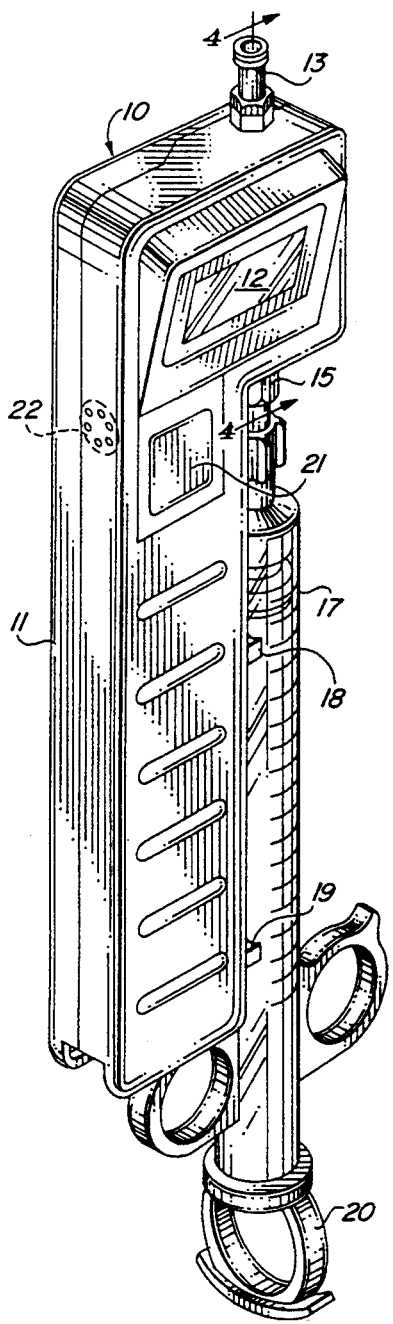
FIG. 1
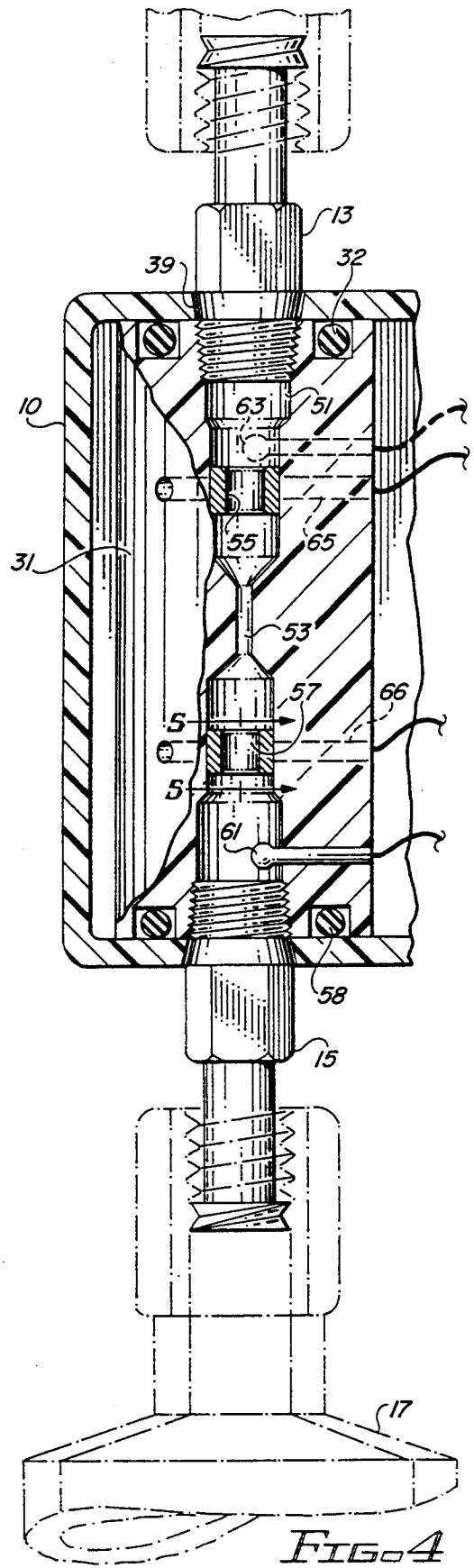
FIG. 5
FIG. 4

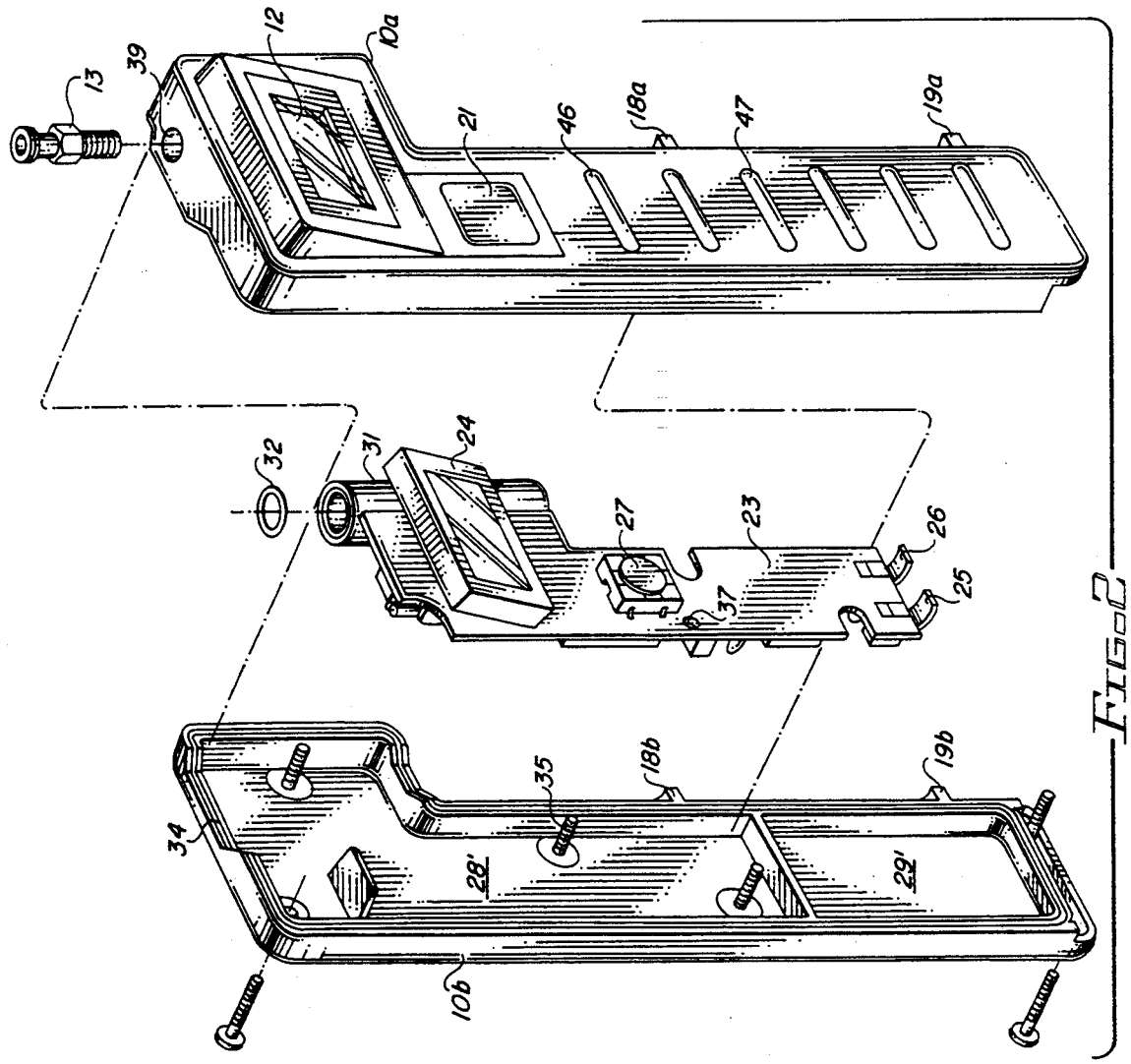

CONDUCTIVITY METER

BACKGROUND OF THE INVENTION

This invention relates to conductivity meters and, in particular, to a meter for accurately and rapidly measuring the conductivity of dialysate.

In the human body, the products of biochemical reactions, known as metabolites, are removed from the blood by diffusion from the blood into the kidneys. If the kidneys fail to function properly, the concentration of metabolites in the blood increases, eventually reaching toxic levels. Metabolites can be removed from the blood by apparatus, known as a hemodialyzer, in which diffusion of metabolites takes place through a semi-permeable membrane separating the blood from an aqueous salt solution known as dialysate.

In general, diffusion depends upon concentration gradient, the difference in concentration between one region and another. Molecules diffuse from a region of higher concentration to a region of lower concentration. A semi-permeable membrane permits only molecules smaller than a predetermined size to pass through the membrane. In a hemodialyzer, the blood is on one side of a membrane and the dialysate is on the other side of the membrane. The dialysate is pumped past the membrane much more quickly than the blood to assure a continuous, fresh supply of dialysate and a high concentration gradient across the membrane, i.e. a very low concentration of metabolites in the dialysate.

A semi-permeable membrane is a two-way street for those molecules which can pass through it. Therefore, the concentration of salts in the dialysate must be carefully monitored to assure that it matches the concentration of salts in the blood, otherwise salts may be added to or removed from the blood unintentionally.

A hemodialysis system produces dialysate by diluting a concentrated salt solution with pure water. The dialysate approximates the salts in human blood, with some salts in higher or lower concentration as determined by a patient's physician. That is, hemodialysis may include adding certain salts, and/or glucose, to the patient's blood during treatment, in addition to removing metabolites from the patient's blood.

Aqueous solutions, particularly aqueous salt solutions, conduct electricity in varying degrees, depending upon the particular salts and the concentration of salt dissolved in the solution. The concentration of salts in dialysate is therefore usually monitored by measuring the conductivity of the dialysate. The pH of the dialysate may be monitored as well. Despite the control systems built into hemodialysis systems, manufacturers typically recommend that the concentration of salt in the dialysate be checked just prior to each patient's hemodialysis.

As known in the art, the conductivity of aqueous solutions is strongly temperature dependent, varying as much as four percent per degree centigrade. For dialysate, the variation is approximately two percent per degree centigrade. Thus, measuring conductivity is not sufficient: one must also measure the temperature of the solution and correct the measurement of conductivity for temperature. Circuitry for measuring conductivity and correcting for temperature is known in the art, e.g. analogue multipliers, analogue to digital converters having a reference voltage which varies with temperature, or a look-up table stored in a memory accessed by a microprocessor. Conductivity is usually expressed as Siemens per square centimeter at 25° C.

For the specific case of dialysate, it is desirable to know the conductivity very accurately. The problem is that making the measurement affects the measurement; i.e. the temperature of the meter can affect the measurement if the temperature of the meter is not the same as the temperature of the dialysate.

U.S. Pat. No. 4,553,552 to Valdespino et al. is premised on an "instantaneous" reading obviating the need to measure temperature, although no experimental data is disclosed substantiating the premise. In the Valdespino et al. patent, the conductivity of dialysate is measured in a syringe filled through a needle inserted into the hemodialysis bath. Because of the large variation in conductivity with temperature, the problem remains of accurately and rapidly measuring the conductivity of dialysate.

In view of the foregoing, it is therefore an object of the invention to provide an improved meter for measuring the conductivity of dialysate.

Another object of the invention is to provide a meter for accurately and rapidly measuring conductivity, thereby minimizing the effect of temperature on the measurement.

A further object of the invention is to provide a flow-through conductivity meter.

Another object of the invention is to provide a conductivity meter which can be left on-line or used separately as a hand-held instrument.

A further object of the invention is to provide an improved cell for measuring the conductivity of a liquid.

SUMMARY OF THE INVENTION

The invention achieves the foregoing objects by providing a conductivity cell having a passageway through which dialysate flows and having a constriction in the passageway for regulating the flow and providing a predetermined cross-sectional area for measuring conductivity. Electrodes for measuring conductivity are located on each side of the constriction. The electrodes are preferably cylindrical, having their longitudinal axes parallel with the passageway. Holes offset from and perpendicular to the longitudinal axis of the cell receive screws which fasten the cell to a printed circuit board and make electrical contact with the electrodes. A thermistor for measuring the temperature of the dialysate is located at either or both ends of the passageway. The printed circuit board contains measurement and display electronics connected to the thermistor and to the electrodes. The cell is made from insulating material, e.g. acetal, and is tapped to receive suitable connectors, such as "luer" connectors, at each end of the passageway. The cell and printed circuit board fit within a housing including a support bracket on the outside thereof for a syringe or other source of vacuum for drawing dialysate through the cell.

BRIEF DESCRIPTION OF THE DRAWINGS

A more complete understanding of the invention can be obtained by considering the following detailed description in conjunction with the accompanying drawings, in which:

FIG. 1 illustrates a conductivity meter constructed in accordance with a preferred embodiment of the invention and using a syringe as a source of vacuum;

FIG. 2 is a partially exploded view of a conductivity meter constructed in accordance with a preferred embodiment of the invention;

FIG. 3 shows the inside of the top portion of the housing for the meter;

FIG. 4 is a cross-section of a conductivity cell constructed in accordance with a preferred embodiment of the invention; and FIG. 5 illustrates a detail of a connection to the conductivity cell.

DETAILED DESCRIPTION OF THE INVENTION

In FIG. 1, housing 10 includes elongated handle 11 and display window 12 in an enlarged portion of housing 10. Display window 12 can be slanted as shown or flat. The enlarged portion of housing 10 extends to one side of handle 11 and terminates at the upper end of the housing. Attached to the upper end of housing 10 is luer connector 13, which is sealed to housing 10 by a taper in connector 13 mating with a countersunk hole in the housing. Attached to the underside of the enlarged portion of housing 10 is luer connector 15, also sealed to the housing. Luer connectors are known in the art for providing a rapid, sealed, fluid coupling in medical and other applications.

Within housing 10, between connectors 13 and 15, is a conductivity cell, not shown in FIG. 1, having a passageway along its longitudinal axis, which is parallel to and displaced from handle 11. Liquid flows through the passageway during the measurement of conductivity. The liquid is drawn through the cell by a source of vacuum, such as syringe 17, attached to one of the connectors. Syringe 17 is attached to luer connector 15 and rests on brackets 18 and 19, which conform to the cylindrical outer surface of syringe 17 to locate the syringe adjacent handle 11. The plunger within syringe 17 is connected to handle 20, which is pulled downward, when oriented as shown in FIG. 1, to draw liquid through the conductivity cell.

Switch cover 21 seals an opening providing access to an on-off switch on a printed circuit board within housing 10. Switch cover 21 can comprise any suitable material such as a small plastic or rubber sheet sealed to the housing. Optional connector 22, shown in dotted line, provides electrical access to the printed circuit board within housing 10 by way of a standard electrical interface such as RS-232 or IEEE-488.

FIG. 2 illustrates in more detail the construction of a conductivity meter in accordance with the invention. Front portion 10a of the housing is shaped to receive printed circuit board 23 having display module 24 attached thereto at an angle to match the angle of window 12. Terminals 25 and 26 provide contacts to a battery, not shown, for powering the circuit on printed circuit board 23. On-off switch 27 is attached to printed circuit board 23 and aligns with cover 21 when the printed circuit board is fitted within the housing. Conductivity cell 31 is mechanically and electrically attached to printed circuit board 23 and has O-rings, such as O-ring 32, at each end thereof for sealing the ends of the cell to the inside of the housing.

The rear edge of front 10a includes raised portion 33 which fits within groove 34 of back 10b. Preferably, groove 34 includes a resilient seal for engaging raised edge 33. The combination of raised edge and recess provide a water and dust tight seal for the interior of the housing. Printed circuit board 23 is attached to front 10a by the frictional engagement of the O-rings around measurement cell 31 and by a screw, not shown, through hole 37. Back 10b is attached to front 10a by a plurality of screws, such as screw 35. After cell 31 is in place, connector 13 is inserted through hole 39 to engage threads at the inside of the end of conductivity cell 31. Connector 15, not shown in FIG. 2, is attached in the same way to the other end of conductivity cell 31. Ribs, such as ribs 46 and 47, on the front surface of front 10a are largely decorative but provide a slight grip for the user. The outside surface of back 10b is flat.

FIG. 3 illustrates the inside of front 10a, showing recesses 28 and 29 which, with recesses 28' and 29' (FIG. 2), provide room for the printed circuit board and a battery. Post 36 includes a central hole or threaded insert for receiving screw 35 (FIG. 2). Post 38 includes a central hole for receiving a screw through hole 37 (FIG. 2) in the printed circuit board. Hole 43, opposite hole 39, receives connector 15, not shown in FIG. 3.

FIG. 4 illustrates in detail the construction of a conductivity cell in accordance with a preferred embodiment of the invention. Cell 31 is a cylinder of insulating material such as acetal or other plastic such as PVC (polyvinylchloride). The particular material used for the body of the cell is not critical so long as the liquid being measured is not a solvent for the particular plastic. In the case of dialysate, any plastic is suitable.

Cell 31 includes longitudinal passageway 51 having several diameters along the length thereof. In particular, constriction 53 located approximately in the middle of cell 31 reduces the diameter of the passageway to a small, but precisely known value, e.g. 0.063 inches. On either side of constriction 53 are electrodes 55 and 57 in a slightly wider portion of the passageway. Electrodes 55 and 57 preferably comprise stainless steel but can be made from a variety of other materials, such as nickel plated copper, titanium-palladium alloy, or graphite. The electrodes are in the shape of cylinders having their axes aligned with passageway 51.

The inside diameter of the electrodes is greater than the diameter of the constriction to increase the surface area of the electrodes. Each end of passageway 51 has yet a larger diameter and is threaded to receive a connector. In addition, cell 31 has a groove at each end, surrounding passageway 51, in which O-rings 32 and 58 are located. These O-rings abut the interior surface of housing 10, sealing passageway 51.

Thermistor 61 is located in a larger diameter portion of passageway 51 for measuring the temperature of the liquid drawn through the passageway. As indicated by dashed lines, thermistor 63 is optionally provided at the opposite end of passageway 51 from thermistor 61. While referred to as a thermistor, it is understood that a thermocouple can be used instead for measuring temperature. While a single thermistor is sufficient, dual thermistors provide redundancy or provide an internal check to be sure that the temperature is being measured accurately.

Electrical contact to electrodes 55 and 57 is made through holes 65 and 66. In a preferred embodiment of the invention, holes 65 and 66 each receive a screw passing through the printed circuit board and entering the holes to contact electrodes 55 and 57. Alternatively, pins on the printed circuit board are inserted through the holes to electrically contact the electrodes and frictionally engage the holes to secure conductivity cell 31 to the printed circuit board. Holes 65 and 66 are skew to the axis of passageway 51. By skew is meant that the holes are not coplaner with the passageway, as illustrated in FIG. 5. In FIG. 5, the longitudinal axis of electrode 55 is in the plane of the drawing and the axis of hole 65 is perpendicular to the plane of the drawing and adjacent electrode 55.

The actual measurement of conductivity is essentially a measurement of the current through the liquid and the voltage drop across the electrodes. This can be done in a variety of ways, known per se in the art, all involving passing an alternating current through the liquid between the electrodes. An alternating current is used rather than a direct current in order to prevent plating of the electrodes. The voltage (V) across the electrodes and the current (I) through the liquid are measured to determine conductivity (I/V). Alternatively, a reference current is used and the voltage is measured or a reference voltage is used and the current is measured.

Since very large or very small voltages or currents are difficult to measure with off-the-shelf electronics, there is a preferred range of voltage and current, e.g. 0.5–5 volts and 1–100 milliamps. The range is due to a desire to avoid expensive or custom electronics, not to something inherently limiting in the measurement process itself.

A conductivity cell is characterized by what is known as cell constant, which indicates the approximate range of conductivities that the cell can measure. The cell constant is approximately determined by the area of the electrodes and their spacing. For example, square electrodes one centimeter on a side separated by one centimeter would have a cell constant of one. Halving the area of the electrodes, or doubling the spacing of the electrodes, halves the cell constant. This is only an approximation since the geometry of the electrodes, and their interaction, as well as the diameter of the constriction, affect cell constant.

In general, one wants a higher cell constant for higher conductivities. The cell is designed to have a resistance that can be measured relatively accurately, e.g. 500–20,000 ohms, for the range of conductivities to be measured. A cell constructed in accordance with the invention has a cell constant of approximately twenty-five. For example, distilled water has a conductivity of less than 1 microSiemen/cm$^2$. If the cell constant were one, the resistance of the cell would be over 1,000,000 ohms with distilled water. Sea water, which contains about four times as much salt as human blood, has a conductivity of about 33,000 microSiemen/cm$^2$. If the cell constant were one, the resistance of the cell would be about thirty ohms with sea water. For a resistance range of 500–20,000 ohms and a cell constant of twenty-five, the range of conductivities which can be very accurately measured is approximately 50,000–1,250 microSiemen/cm$^2$.

In operating the meter, handle 20 is withdrawn from syringe 17, drawing liquid through passageway 51. The temperature of the liquid in the passageway varies when initially drawn through the passageway. However, after a few seconds, the thermistor stabilizes, i.e. warms to the temperature of the liquid. The conductivity is then corrected for temperature and displayed. The entire measurement takes approximately four seconds and only a few cubic centimeters of liquid are necessary: a ten cc. syringe is more than enough for measuring dialysate.

The conductivity cell of FIG. 4 is incorporated into a hand-held unit as shown or is installed permanently in a hemodialysis system. The cell enables one to carefully control cell constant by changing the size of constriction 53, the size of electrodes 55 and 57, the spacing of the electrodes, and the material for the electrodes. For example, graphite electrodes have a spongy texture, providing a larger surface area than smooth electrodes of the same dimensions. Thus, cells of the same outside dimensions can accommodate a variety of conductivity ranges.

A cell constructed in accordance with the invention had an outside diameter of 0.5 inches, a length of 1.756 inches, an inside diameter at the constriction of 0.063 inches, an inside diameter of 0.246 inches at the ends, and an inside diameter of 0.202 inches at the electrodes. The electrodes had an inside diameter of 0.182 inches, a length of 0.35 inches, and a center-to-center spacing of 0.70 inches. Varying the parameters described, a cell constant in the range of one to one hundred can be obtained from a cell having the same length and outside diameter.

While described in a preferred embodiment as a conductivity meter for dialysate, it is understood that the conductivity cell of the invention can be applied to any liquid. For example, TDS (total dissolved solids) is an important parameter in the care of swimming pools. A small sample of water can be drawn through the cell and the conductivity of the water measured. Since a hose of any desired length can be attached to the cell, one can sample surface water or water at the bottom of a pool or pond with equal ease. With a pH cell instead of a conductivity cell, the pH of the pool water or other liquid can be measured.

Having thus described the invention it will be apparent to those of skill in the art that various modifications can be made within the scope of the invention. For example, luer connectors are not the only type of connector which can be used. They are preferred because they are common in the medical environment and are plastic, conducting little heat to or from the liquid. While the passageway is shown and described a having five diameters, it is understood that other combinations of diameters can be used. The inside diameters of the ends are determined by the connectors to be attached. The intermediate diameters are determined by the outside diameters of the electrodes. The electrodes could be made thicker to fit the outer diameters of the passageway, reducing the number of diameters to three. The electrodes need not be hollow with the liquid flowing through them. A solid electrode, such as a pin or screw, around or across which the liquid flowed could be used instead. The thermistor is preferably located near or between the electrodes. If the electrodes were sufficiently thick, the thermister could be located in an electrode.

I claim:

1. A meter for measuring conductivity of a liquid, said meter comprising:
    a conductivity cell including a cylindrical member having a passageway through which said liquid can flow, said passageway extending longitudinally through said member and having a constriction of predetermined diameter;
    a first electrode in said passageway on one side of said constriction;
    a second electrode in said passageway, wherein said constriction is between said first electrode and said second electrode along said passageway;

a pair of holes through said member, said holes being skew to said passageway and adjacent respective ones of said first and second electrodes;

a thermistor in said passageway adjacent one of said electrodes; and circuit means connected to said first electrode, said second electrode, and to said thermistor for measuring the temperature and the conductivity of said liquid.

2. The meter as set forth in claim 1 wherein said circuit means includes a printed circuit board having a pair of terminal corresponding to said holes.

3. The meter as set forth in claim 2 and further comprising screws through respective ones of said holes and said terminals mechanically and electrically connecting said cell to said printed circuit board.

4. The meter as set forth in claim 2 and further comprising pins through respective ones of said holes and said terminals mechanically and electrically connecting said cell to said printed circuit board.

5. The meter as set forth in claim 1 and further comprising means attached to one end of said passageway for drawing said liquid through said passageway.

6. The meter as set forth in claim 5 wherein said means for drawing said liquid through said passageway comprises a syringe.

7. The meter as set forth in claim 6 wherein said syringe is attached to the end of said passageway nearer said thermistor.

8. A method for measuring conductivity of a liquid, the method comprising the steps of:

providing a conductivity cell through which said liquid can flow;

drawing said liquid through said cell;

monitoring the temperature of said liquid while it is drawn through said cell;

measuring the conductivity of said liquid when the temperature of said liquid stabilizes while continuing to draw said liquid through said cell; and correcting the measured conductivity to a reference temperature.

9. The method as set forth in claim 8 wherein said measuring step comprises measuring the conductivity of said liquid when consecutive temperature measurements indicate the same temperature while continuing to draw said liquid through said cell.

10. A meter for measuring the properties of a liquid, said meter comprising:

a housing having an elongated handle and an enlarged portion extending to one side of said handle, said enlarged portion terminating at a first end of said housing;

a flow through measuring cell in said enlarged portion, said cell having a longitudinal axis parallel to and displaced from said handle;

a first connector attached to said first end and to said cell;

a second connector attached to said enlarged portion and to said cell;

said connectors providing access to said flow through measuring cell through said housing; and circuit means within said handle and connected to said cell for measuring a property of said liquid.

11. The meter as set forth in claim 10 and further comprising:

a syringe, attached to said second connector, for drawing liquid through said cell; and at least one bracket on said handle, said bracket locating said syringe adjacent said handle.

* * * * *